(12) United States Patent
Pichereau-Basle

(10) Patent No.: US 11,202,565 B2
(45) Date of Patent: Dec. 21, 2021

(54) METHOD AND DEVICE FOR INTERMEDIATE ASSESSMENT OF AN EYE

(71) Applicant: SiVIEW, Marcoussis (FR)

(72) Inventor: Laure Pichereau-Basle, Marcoussis (FR)

(73) Assignee: SiVIEW, Marcoussis (FR)

( * ) Notice: Subject to any disclaimer, the term of this patent is extended or adjusted under 35 U.S.C. 154(b) by 215 days.

(21) Appl. No.: 16/464,073

(22) PCT Filed: Nov. 27, 2017

(86) PCT No.: PCT/EP2017/080499
§ 371 (c)(1),
(2) Date: May 24, 2019

(87) PCT Pub. No.: WO2018/096140
PCT Pub. Date: May 31, 2018

(65) Prior Publication Data
US 2019/0380575 A1   Dec. 19, 2019

(30) Foreign Application Priority Data

Nov. 28, 2016   (FR) ..................................... 1661568

(51) Int. Cl.
*A61B 3/103*   (2006.01)
*A61B 3/00*    (2006.01)

(52) U.S. Cl.
CPC ............ *A61B 3/103* (2013.01); *A61B 3/0041* (2013.01)

(58) Field of Classification Search
CPC ..... A61B 3/103; A61B 3/0047; A61B 3/0285; A61B 3/028; A61B 3/036; A61B 3/04; A61B 3/1035; A61B 3/10; A61B 3/02; A61B 3/032; G02C 13/005
USPC ................. 351/205, 211, 216, 217, 218, 246
See application file for complete search history.

(56) References Cited

U.S. PATENT DOCUMENTS

| | | | |
|---|---|---|---|
| 5,914,772 A | 6/1999 | Dyer | |
| 2006/0152675 A1* | 7/2006 | Toshima | A61B 3/032 351/205 |
| 2016/0029885 A1* | 2/2016 | Hoof | A61B 3/0285 351/234 |

FOREIGN PATENT DOCUMENTS

| | | |
|---|---|---|
| JP | 2011-013373 A | 1/2011 |
| WO | WO 2016/084086 A1 | 6/2016 |

OTHER PUBLICATIONS

Benjamin, W. J., "Chapter 20: Monocular and Binocular Subjective Refraction," Borish's Clinical Refraction ($2^{nd}$ Edition), (2006), pp. 790-872.

Grosvenor, T., "Chapter 9: Subjective Refraction," Primary Care Optometry ($5^{th}$ Edition), (2007), pp. 285-299.

(Continued)

*Primary Examiner* — Travis S Fissel
(74) *Attorney, Agent, or Firm* — Pillsbury Winthrop Shaw Pittman LLP

(57) ABSTRACT

A method for intermediate assessment of an eye, whereby an intermediate assessment is carried out making it possible to adapt and optimise a subsequent full assessment. The preliminary assessment takes slightly more time initially but provides for greater efficiency in carrying out the subsequent full assessment by preventing the performance of operations or calculations that are unsuccessful.

8 Claims, 3 Drawing Sheets

(56) References Cited

OTHER PUBLICATIONS

Watt, W. S., "How Visual Acuity is Measured," Home About Resources News & Info Publications Contact Writings, Oct. 2003, XP055399156, 4 pages, Retrieved from the Internet: URL:http://lowvision.preventblindness.org/ eye-conditions/how-visual-acuity-is-measured/>, [retrieved on Aug. 16, 2017].
International Search Report as issued in International Patent Application No. PCT/EP2017/080499, dated Mar. 22, 2018.

* cited by examiner

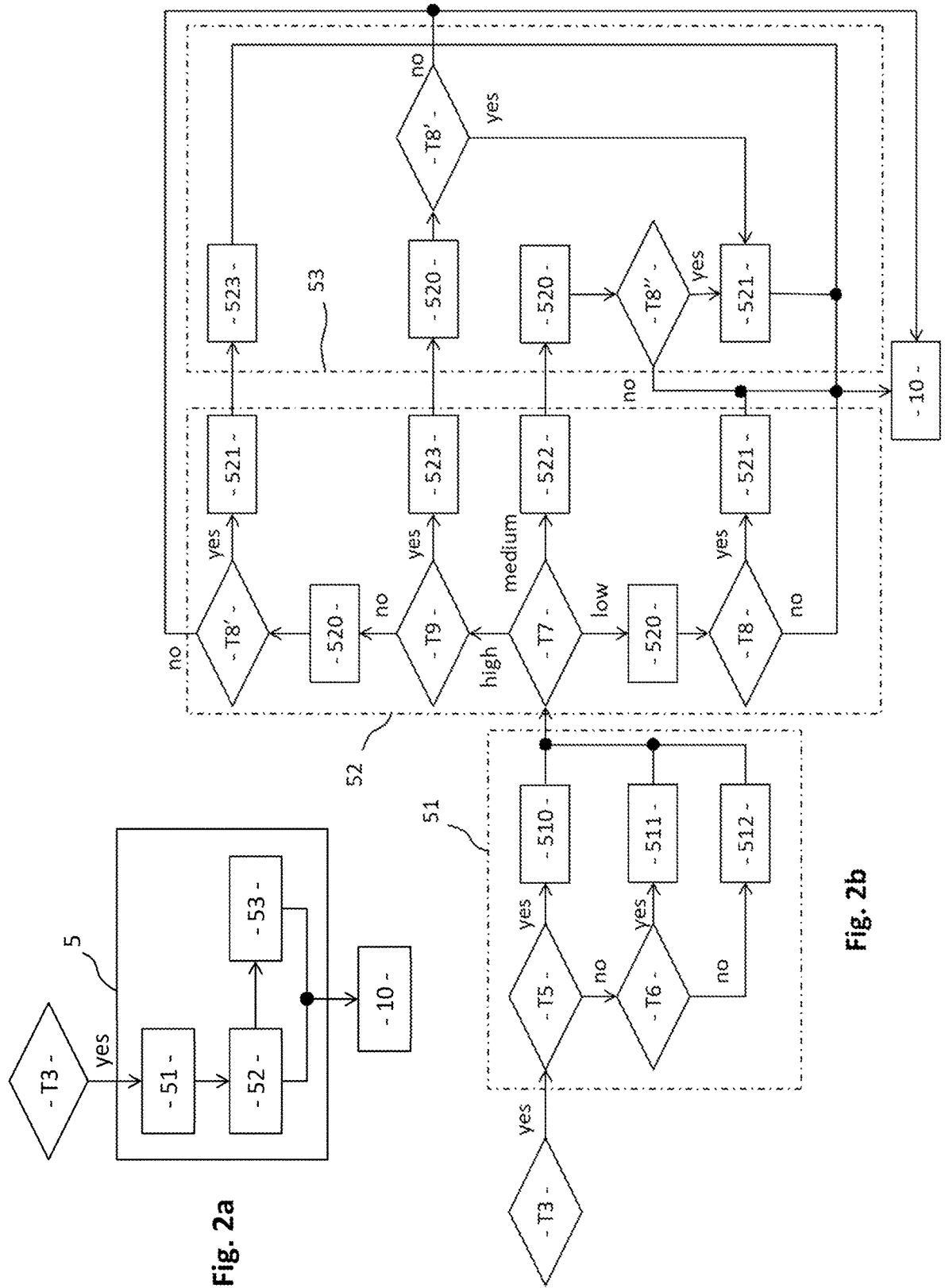

METHOD AND DEVICE FOR INTERMEDIATE ASSESSMENT OF AN EYE

CROSS REFERENCE TO RELATED APPLICATIONS

This application is the U.S. National Stage of PCT/EP2017/080499, filed Nov. 27, 2017, which in turn claims priority to French Patent Application No. 1661568 filed Nov. 28, 2016, the entire contents of all applications are incorporated herein by reference in their entireties.

TECHNICAL FIELD OF THE INVENTION

The technical field of the invention is that of the characterisation of optical systems. The present invention relates to a method and a device for intermediate assessment of an eye being able in particular to be used to carry out later a sight test.

TECHNOLOGICAL BACKGROUND OF THE INVENTION

A sight test is generally carried out on a user to determine if he needs a correction, and if needs be, the type of said correction. The correction is then typically provided via a pair of glasses or contact lenses.

The starting point of the sight test is an objective refraction measurement which is generally carried out by means of an autorefractometer or which may be, by default, the preceding correction of the user. Alternatively to the use of an autorefractometer, a manual skiascopy technique is sometimes used. The objective refraction value measured with the autorefractometer is not directly usable for a prescription for the following reasons:
- it is often too high, especially in young subjects with an over evaluation of myopia and an under-evaluation of hypermetropia;
- it often shows up slight tension astigmatisms which should not be prescribed;
- it does not make it possible to determine if the subject sees clearly and in a comfortable manner with his correction;
- in certain rare cases, it may turn out to be completely false.

The visual examination thus continues with a subjective refraction measurement, which includes the following steps:
1) monocular step,
2) biocular step,
3) binocular step.

The monocular step comprises the following steps:
a) search for the myopia or hypermetropia value, designated "sphere value at the level",
b) search for the astigmatism value, with its axis and its power,
c) if the astigmatism is modified, verification of the sphere value obtained previously.

The monocular step is carried out firstly for one eye, then for the other eye. The biocular step and the binocular step are each carried out for both eyes at the same time.

The subjective refraction is carried out by a practitioner interacting with the subject.

In order to test different corrections for the subject, the practitioner uses suitable equipment, which may be:
- a pair of test glasses with test lenses,
- a manual refractor head,
- an automatic refractor head.

In the first case, the practitioner manually changes the test lenses of the pair of test glasses. With a refractor head, the practitioner successively places different glasses in front of the eyes of the subject, using rotary wheels in the case of a manual refractor head or via a control console in the case of an automatic refractor head.

In order to carry out visual tests more quickly than in the prior art, the U.S. Pat. No. 5,914,772 proposes a method in which the subjective refraction measurement is replaced by new automatic measurement steps. This method turns out however to be less precise and repeatable than the methods of the prior art, notably in the case of astigmatism.

SUMMARY OF THE INVENTION

The invention offers a solution to the aforementioned problems, by proposing an intermediate assessment that can be used to carry out later a visual test more quickly than in the prior art, while being at least as precise and repeatable.

A first aspect of the invention relates to a method for intermediate assessment of an eye of a user comprising:
- a step of attributing to the eye of the user a reference visual acuity value AVR, as a function of the age of the user and an initial set of parameters M1 of the eye comprising an initial sphere value SPH1, an initial cylinder value CYL1 and an initial cylinder axis value AX1, and by means of a matrix having a plurality of L lines and a plurality of C columns and thus comprising L×C components, each line corresponding to a set of parameters category, each column corresponding to an age category and each component being associated with a reference visual acuity value AVR;
- if the sphere value SPH1 of the initial set M1 is such that:

$-5.00$ dioptres$\leq SPH1 \leq +3.00$ dioptres, a step of acquisition of a raw visual acuity value AVB of the eye;
- if the raw visual acuity value AVB has been measured beforehand and if it is greater than a reference raw visual acuity value AVBR, a step of weighting the initial set of parameters M1 to obtain a weighted set of parameters M1' having the initial cylinder value CYL1, the initial cylinder axis value AX1 and a weighted sphere value SPH1' such that:

$SPH1+0.25$ dioptre$\leq SPH1' \leq SPH1+0.75$ dioptre;

- a step of acquisition of a modified visual acuity value AVM of the eye, by arranging in front of the eye an optic having the initial set of parameters M1 or, if needs be, the weighted set of parameters M1';
- if the modified visual acuity value AVM is strictly less than the reference visual acuity value AVR, an step of adjustment comprising at least one acquisition of an adjusted visual acuity value AVA of the eye, by arranging in front of the eye an optic having an adjusted set of parameters M2.

The visual acuity of an eye quantifies its capacity to discern a detail and is measured both far and near. The visual acuity of the eye is measured by searching for the smallest possible angle under which the eye distinguishes said detail, which is generally a letter, a character or a figure that is also called optotype. The optotype is placed at a given distance and its dimensions are progressively decreased. For example, in distance vision, the optotype is placed in France at five metres and in Anglo-Saxon countries at six metres. The smallest possible angle under which the eye sees the optotype is called the minimum resolution angle and the visual acuity of the eye is defined as the inverse of this minimum resolution angle. The more the eye is capable of distinguishing optotypes under a small angle, the greater its visual acuity.

Thanks to the method according to the first aspect of the invention, an intermediate assessment is carried out to make it possible to adapt and to optimise a later full assessment. The preliminary assessment initially requires a little additional time but next enables great efficiency in the carrying out of the later full assessment, while avoiding carrying out manipulations or calculations that are not successful.

The method for intermediate assessment of an eye of a user according to an aspect of the invention cannot replace a subjective refraction measurement of a visual test. It is not necessary for the production of a prescription for a visual correction; it is not sufficient either for producing a prescription for a visual correction.

Apart from the characteristics that have been evoked in the preceding paragraph, the method for intermediate assessment of an eye according to the first aspect of the invention may have one or more additional characteristics among the following, considered individually or according to all technically possible combinations thereof:

After each acquisition of an adjusted visual acuity value AVA of the eye, if the adjusted visual acuity value AVA measured for the eye is greater than or equal to the reference visual acuity value AVR, the step of adjustment ends.

If, with an optic having a set of parameters of which the sphere value has a positive variation compared to the preceding tested sphere value, or of which the axis value has a variation compared to the preceding tested axis value, or of which the cylinder and axis values correspond respectively to an expected total value ATA, the adjusted visual acuity value AVA acquired for the eye is greater than or equal to the reference visual acuity value AVR, then the method comprises a step according to which an acquisition is made of a visual acuity value of the eye by increasing by +0.75 dioptre the sphere value of the optic.

The step of adjustment comprises a first sub-step in which a low or medium cylinder category and a high cylinder category, a low sphere category and a high sphere category are distinguished, and according to which:

if the cylinder is high, at the most four acquisitions are made of an adjusted visual acuity value AVA of the eye by varying the cylinder axis value of the optic;

if the cylinder is low or medium and if the sphere is high, at the most four acquisitions are made of an adjusted visual acuity value AVA of the eye by varying the sphere value of the optic;

if the cylinder is low or medium and if the sphere is low, at the most two acquisitions are made of an adjusted visual acuity value AVA of the eye by varying the sphere value of the optic.

The step of adjustment comprises a second sub-step such that:

if the cylinder is low, a comparison is made of the cylinder and the axis with an expected total value ATA respectively for the cylinder and the axis; if the cylinder has a power difference greater than or equal to 0.75 dioptre with its expected total value ATA and/or if the axis has a difference greater than or equal to 25° with its expected total value ATA, then an acquisition is made of an adjusted visual acuity value AVA of the eye using the expected total value ATA for the cylinder and the axis of the optic;

if the cylinder is medium, at the most two acquisitions are made of an adjusted visual acuity value AVA of the eye by varying the axis value of the optic;

if the cylinder is high and if the sphere value SPH1 or weighted sphere value SPH1' is strictly greater than the cylinder value CYL1, at the most four acquisitions are made of the adjusted visual acuity value AVA of the eye by varying the sphere value of the optic;

if the cylinder is high and if the sphere value SPH1 or weighted sphere value SPH1' is less than or equal to the cylinder value CYL1, a comparison is made of the cylinder and the axis with the expected total value ATA for the cylinder and the axis; if the cylinder has a power difference greater than or equal to 1.50 dioptres with its expected value ATA and/or if the axis has a difference greater than or equal to 20° with its expected total value ATA, then an acquisition is made of an adjusted visual acuity value AVA of the eye using the expected total value ATA for the cylinder and the axis of the optic.

If the cylinder is low, the step of adjustment is terminated at the end of the first and second sub-steps, if not the step of adjustment comprises a third sub-step such that:

if the cylinder is medium, a comparison is made of the cylinder and the axis with their expected total value ATA; if the cylinder has a power difference greater than or equal to 1.00 dioptre with its expected total value ATA and/or if the axis has a difference greater than or equal to 15° with its expected total value ATA, then an acquisition is made of an adjusted visual acuity value AVA of the eye using the expected total value ATA for the cylinder and the axis of the optic;

if the cylinder is high and if the sphere value SPH1 or weighted sphere value SPH1' is strictly greater than the cylinder value CYL1, a comparison is made of the cylinder and the axis with their expected total value ATA; if the cylinder has a power difference greater than or equal to 1.50 dioptres with its expected total value ATA and/or if the axis has a difference greater than or equal to 20° with its expected total value ATA, then an acquisition is made of an adjusted visual acuity value AVA of the eye using the expected total value ATA for the cylinder and the axis of the optic;

if the cylinder is high and if the sphere value SPH1 or weighted sphere value SPH1' is less than or equal to the cylinder value CYL1, at the most four acquisitions are made of an adjusted visual acuity value AVA of the eye by varying the sphere value of the optic.

A second aspect of the invention relates to a computer programme product comprising software instructions which, when the programme is executed by a computer, implement the method according to the first aspect of the invention. The computer programme including instructions executable by a machine for implementing the method according to the first aspect of the invention may be implemented by a computer including at least one interface, a processor and a non-transitory physical memory, also designated in a general manner as being a non-transitory support readably by computer or a non-transitory storage memory. The computer is a special purpose computer, given that it is programmed for executing the specific steps of the method described in the present document. The non-transitory memory is encoded or programmed with specific code instructions for implementing the method described in the present document and the steps that are associated therewith. The non-transitory memory communicates with the physical processor such that the physical processor, when it is used, reads and executes the specific code instructions that are integrated in the non-transitory memory. The interface of the special purpose computer communicates with the physical processor and receives input parameters that are processed by the physical processor A third aspect of the invention relates to a recording support readable by a computer, on which is recorded the computer programme product according to the second aspect of the invention. Various forms of recording support readable by computer may be used for the execution of one or more sequences of one or more instructions by the processor. The term "recording support readable by computer", such as used here, refers to any support participating in providing instructions to a processor for the execution of said instructions. Such a support may take numerous forms, including, in a non-limiting manner: non-volatile supports, volatile supports and transmission supports. Non-volatile supports include, for example, optic or magnetic discs. Volatile supports include, for example, dynamic memories. Transmission supports include, for example, coaxial cables, copper wires and optic fibres. Common forms of support readable by computer include, for example, a diskette, a floppy disk, a hard disk, a magnetic tape or any other magnetic support, a CD-ROM, a DVD or any other optic support, perforated cards, paper strips or any other physical support with hole patterns, a RAM, a PROM, an EPROM, a FLASH-EPROM memory or any other memory chip or cartridge, a carrier wave, and any other support from which a computer can read.

A fourth aspect of the invention relates to a device for intermediate assessment of an eye comprising:
   a memory for storing a matrix having a plurality of L lines and a plurality of C columns and thus comprising L×C components, each line corresponding to a set of parameters category, each column corresponding to an age category and each component being associated with a reference visual acuity value AVR,
   a memory for storing a set of parameters comprising a sphere value, a cylinder value and a cylinder axis value,
   a plurality of optics,
   a means for arranging an optic of the plurality of optics in front of the eye,
   a display means,
   a means for acquiring visual acuity values of the eye,
   a memory for storing an acquired visual acuity value,
   a calculator comprising means for carrying out the steps of the method for intermediate assessment of an eye according to the first aspect of the invention.

Each optic of the plurality of optics has, compared to the initial set of parameters M1 of the eye, an adjusted set of parameters M2 comprising a sphere value SPH2, a cylinder value CYL2 and a cylinder axis value AX2. The adjusted set of parameters M2 evolves at each adjustment. The optics of the plurality of optics thus do not all have the same adjusted set of parameters M2.

The invention and its different applications will be better understood on reading the description that follows and by examining the figures that accompany it.

BRIEF DESCRIPTION OF THE FIGURES

The figures are presented for indicative purposes and in no way limit the invention.

FIG. 2a shows a first schematic representation of the sub-steps of a step of adjustment of the intermediate assessment of FIG. 1a.

FIG. 2b shows a second schematic representation, in detail, of the sub-steps of the step of adjustment of FIG. 2a.

DETAILED DESCRIPTION OF AT LEAST ONE EMBODIMENT OF THE INVENTION

Unless stated otherwise, a same element appearing in the different figures has a single reference.

Figure 1:
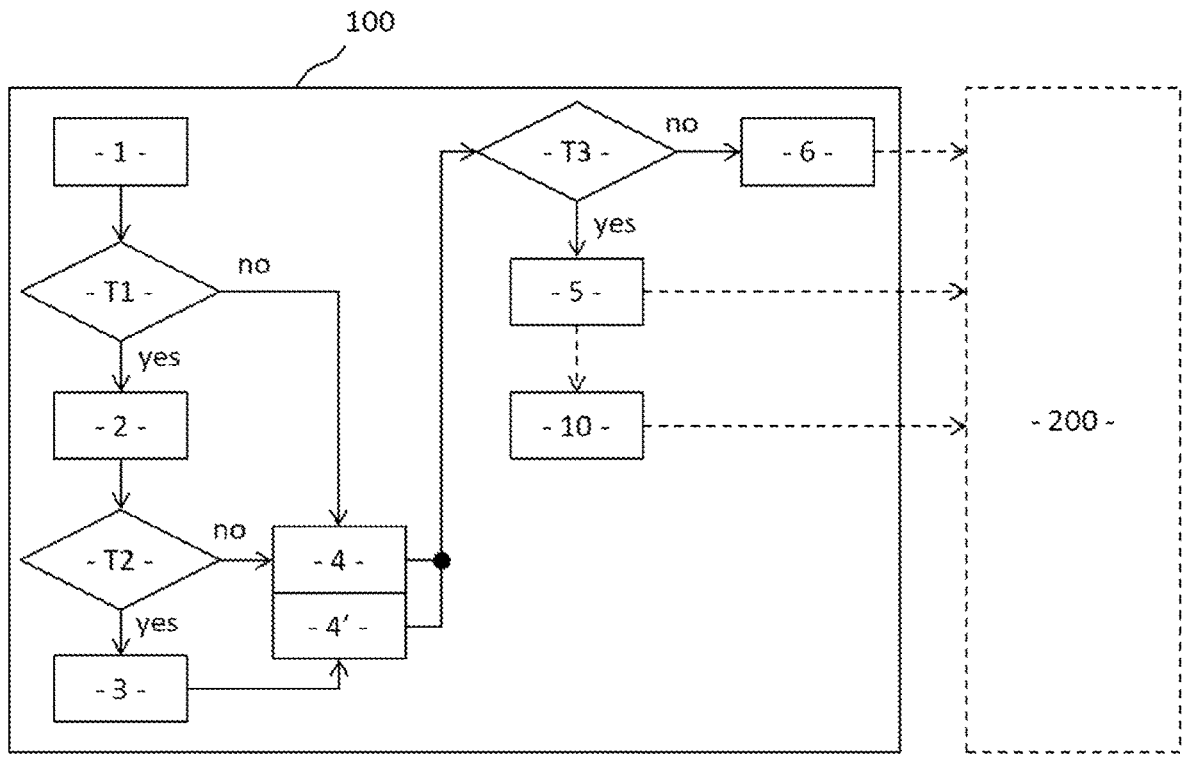
FIG. 1 shows a schematic representation of a method for intermediate assessment of an eye according to an embodiment of the invention.

FIG. 1 shows a schematic representation of a method 100 for intermediate assessment of an eye according to an embodiment of the invention. The method 100 is preferentially implemented by means of an intermediate assessment device (not represented) including:
   a first memory for storing a matrix having a plurality of L lines and a plurality of C columns and thus comprising L×C components, each line corresponding to a set of parameters category, each column corresponding to an age category and each component being associated with a reference visual acuity value AVR,
   a second memory for storing an age datum and a set of parameters comprising a sphere value, a cylinder value and a cylinder axis value,
   a plurality of optics,
   a means for arranging an optic of a plurality of optics in front of the eye: this means is preferentially an automatic refractor head, but may alternatively be a manual refractor head or a pair of test glasses with test lenses,
   a distance vision display means, preferably comprising a screen, polarised or not, or alternatively a projector or a cardboard scale;
   a means for acquiring visual acuity values of the eye,
   a third memory for storing an acquired visual acuity value,
   a calculator comprising means for carrying out the steps of the method 100 for intermediate assessment of an eye.

The first, second and third storage memories may be first, second and third parts of a same storage memory. Alternatively, the first, second and third storage memories may each form a distinct storage memory.

The method 100 includes a step 1 according to which the calculator attributes a reference visual acuity value AVR to the eye. The calculator uses for this an age datum of the eye and an initial set of parameters M1 comprising:
   an initial sphere value SPH1,
   an initial cylinder value CYL1 and
   an initial cylinder axis value AX1.

The age datum and/or the initial set of parameters may be provided to the intermediate assessment device via:
   an objective measurement, or
   an input via a human-machine interface such as a keyboard, or
   a reading of the second storage memory.

An objective refraction measurement via an autorefractometer or an auto-refractokeratometer may make it possible to obtain the initial set of parameters. Alternatively, an initial set of parameters corresponding to a former prescription may be input. According to another alternative, a set of parameters resulting from a preceding intermediate assessment and recorded in the second storage memory may be read and used as initial set of parameters during a new intermediate assessment.

The method 100 next includes a step of test T1 according to which the calculator answers the following question: is the initial sphere value SPH1 such that:

−5.00 dioptres≤SPH1≤+3.00 dioptres?

If no, the following step of the method 100 is a step 4 according to which a modified visual acuity value AVM of the eye is acquired, by arranging in front of the eye an optic having the initial set of parameters M1.

If yes, the following step of the method 100 is a step 2 according to which a raw visual acuity value AVB of the eye is acquired. No optic is placed in front of the eye during step 2.

Step 2 is followed by a step of test T2 according to which the calculator answers the following question: is the raw visual acuity value AVB strictly greater than a reference raw visual acuity value AVBR? The raw visual acuity value AVBR is a reference raw visual acuity value AVBR which is for example obtained from the initial set of parameters M1 and from a known rule called Swaine's rule.

If the raw visual acuity value AVB is less than or equal to the reference raw visual acuity value AVBR, the following step of the method 100 is step 4 described previously.

If the raw visual acuity value AVB is strictly greater than the reference raw visual acuity value AVBR, the following step of the method 100 is a step 3 according to which the calculator weights the initial set of parameters M1 to obtain a weighted set of parameters M1' having the initial cylinder value CYL1, the initial cylinder axis value AX1 and a weighted sphere value SPH1' such that:

SPH1+0.25 dioptre≤SPH1'≤SPH1+0.75 dioptre

Step 3 is followed by a step 4' according to which a modified visual acuity value AVM' of the eye is acquired, by arranging in front of the eye an optic having the weighted set of parameters M1'.

Step 4 or step 4' are followed by a step of test T3 according to which the calculator answers the following question: is the modified visual acuity value AVM, AVM' of the eye strictly less than the reference visual acuity value AVR of the eye?

if the answer is no, the intermediate assessment method 100 preferentially comprises a step 6 according to which an acquisition is made of a visual acuity value of the eye by increasing by +0.75 dioptre the starting sphere value SPH1, SPH1' of the optic. Step 6 corresponds to an accommodation verification, then the intermediate assessment method 100 is terminated. It is preferentially followed by a full assessment method 200, described hereafter.

If the answer is yes, the following step of the method 100 is a step of adjustment according to which at least one adjusted visual acuity value AVA of the eye is acquired, by arranging in front of the eye an optic having an adjusted set of parameters M2. Each adjustment uses as starting point the initial set of parameters M1 (SPH1, CYL1, AX1) or, if the step of weighting 3 has taken place, the weighted set of parameters M1' (SPH1', CYL1, AX1). In the detailed description of the step of adjustment 5, hereafter, the expression "starting sphere value SPH1, SPH1'" is used to designate the initial sphere value SPH1 or, if the step of weighting 3 has taken place, the weighted sphere value SPH1'.

Figure 2C:
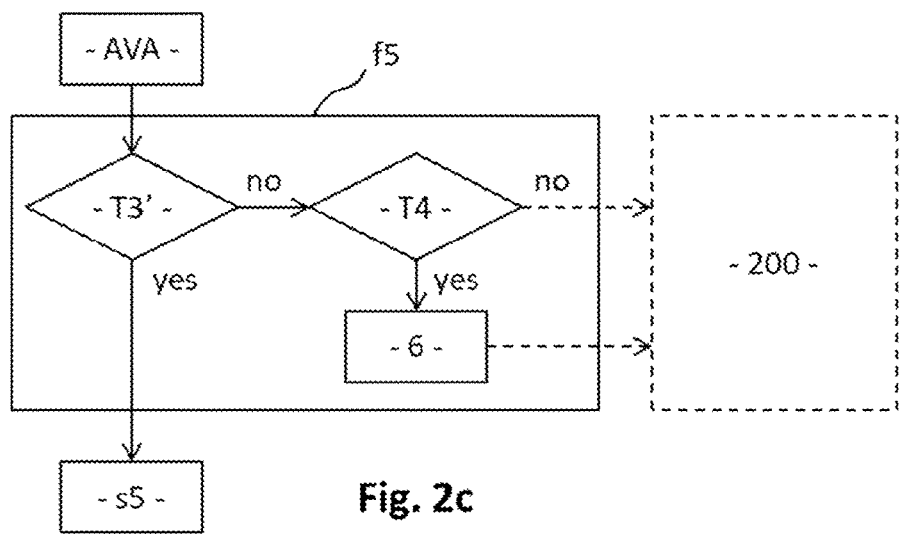
FIG. 2c shows a schematic representation of a test step carried out after each acquisition of an adjusted visual acuity value, in the course of the step of adjustment of FIGS. 2a and 2b.

FIG. 2c shows a schematic representation of a step f5 which is advantageously carried out after each acquisition of an adjusted visual acuity value AVA of the eye, in the course of the step of adjustment 5 (reference "AVA" in FIG. 2c). Step f5 comprises a sub-step of test T3' according to which the calculator answers the question: is the adjusted visual acuity value AVA of the eye strictly less than the reference visual acuity value AVR of the eye?

If the answer is yes, the step of adjustment 5 continues (reference "s5" in FIG. 2c).

if the answer is no, the step of adjustment 5 is terminated. According to an embodiment, step f5 and the intermediate assessment method 100 are also terminated. According to another embodiment, step f5 advantageously comprises a sub-step of test T4 according to which the calculator answers the question: does the sphere value of the optic have a positive variation compared to the starting sphere value SPH1, SPH1', or does the axis value of the optic have a variation compared to the initial axis value AX1, or do the cylinder and axis values of the optic correspond respectively to an expected total value ATA?

if the answer is yes, step f5 comprises step 6 described previously, according to which an acquisition is made of a visual acuity value of the eye by increasing by +0.75 dioptre the starting sphere value SPH1, SPH1' of the optic. It may be noted that step 6 is carried out systematically at the end of test T4, except when the sphere value of the optic has a negative variation compared to the starting sphere value SPH1, SPH1'. Step 6 corresponds to an accommodation verification. Step f5 and the intermediate assessment method 100 are next terminated, if the answer is no, step f5 and the intermediate assessment method 100 are terminated.

Step f5 makes it possible to interrupt the intermediate assessment method 100 as soon as the adjusted visual acuity value AVA of the eye is greater than or equal to the reference value AVR.

If the reference visual acuity value AVR has not been reached at the end of the step of adjustment 5, the intermediate assessment method 100 advantageously continues with a step 10 according to which an acquisition is made of a visual acuity value of the eye by arranging in front of the eye an optic which is a pinhole disk. The intermediate assessment method 100 is next terminated. It is advantageously followed by a full assessment method 200, described later.

The step of adjustment 5 will now be described in a detailed manner, in relation with FIGS. 2a and 2b. FIG. 2a shows a first schematic representation of the sub-steps of an step of adjustment of the intermediate assessment of FIG. 1a. FIG. 2b shows a second schematic representation, in detail, of the sub-steps of the step of adjustment of FIG. 2a.

The step of adjustment 5 comprises a first sub-step 51 followed by a second sub-step 52. At the end of the second sub-step 52:

either the step of adjustment 5 is terminated, or the step of adjustment 5 continues with a third sub-step 53, then the step of adjustment 5 is terminated.

The first sub-step 51 preferentially comprises a test T5 according to which the calculator answers the question: is the initial cylinder value CYL1 high?

if the answer is yes, a step 510 is carried out according to which at the most four acquisitions of an adjusted visual acuity value AVA of the eye are made, by varying the cylinder axis value of the optic compared to the initial value AX1. The first sub-step 51 is next terminated.

if the answer is no, a test T6 is carried out according to which the calculator answers the question: is the starting sphere value SPH1, SPH1' high?

if the answer is yes, a step 511 is carried out according to which at the most four acquisitions of an adjusted visual acuity value AVA of the eye are made, by varying the sphere value of the optic compared to the starting sphere value SPH1, SPH1'. The first sub-step 51 is next terminated.

if the answer is no, a step 512 is carried out according to which at the most two acquisitions of an adjusted visual acuity value AVA of the eye are made, by varying the sphere value of the optic compared to the starting sphere value SPH1, SPH1'. The first sub-step 51 is next terminated.

Each acquisition carried out during step 510 uses an adjusted set of parameters M2 for the optic, having:
a sphere value SPH2 equal to the starting sphere value SPH1, SPH1', and
a cylinder value CYL2 equal to the initial cylinder value CYL1.

During the first acquisition of step 510, the cylinder axis value AX2 of the adjusted set of parameters M2 preferentially has a variation of +5° compared to the initial cylinder axis value AX1:

$$AX2=AX1+5°$$

Step f5 described previously next takes place, which determines if the step of adjustment 5 continues or is terminated. If the step of adjustment 5 continues, a second acquisition of step 510 is made with a cylinder axis value AX2 of the adjusted set of parameters M2 which preferentially has a variation of −5° compared to the initial cylinder axis value AX1:

$$AX2=AX1-5°$$

Step f5 next takes place. If the step of adjustment 5 continues at the end of step f5, a third acquisition of step 510 is made with a cylinder axis value AX2 of the adjusted set of parameters M2 which preferentially has a variation of +15° compared to the initial cylinder axis value AX1:

$$AX2=AX1+15°$$

Step f5 next takes place. If the step of adjustment 5 continues at the end of step f5, a fourth acquisition of step 510 is made with a cylinder axis value AX2 of the adjusted set of parameters M2 which preferentially has a variation of −15° compared to the initial cylinder axis value AX1:

$$AX2=AX1-15°$$

Step f5 next takes place. If the step of adjustment 5 is not terminated at the end of step f5, the step of adjustment 5 continues with the second sub-step 52.

Each acquisition carried out during step 511 uses an adjusted set of parameters M2 for the optic, having:
a cylinder value CYL2 equal to the initial cylinder value CYL1, and
a cylinder axis value AX2 equal to the initial cylinder axis value AX1.

During the first acquisition of step 511, the sphere value SPH2 of the adjusted set of parameters M2 preferentially has a first positive variation compared to the starting sphere value SPH1, SPH1':

$$SPH2=(SPH1,SPH1')+k1 \text{ dioptre}$$

Step f5 described previously next takes place, which determines if the step of adjustment 5 continues or is terminated. If the step of adjustment 5 continues, a second acquisition of step 511 is carried out with a sphere value SPH2 of the adjusted set of parameters M2 which preferentially has a first negative variation compared to the starting sphere value SPH1, SPH1':

$$SPH2=(SPH1,SPH1')-k1 \text{ dioptre}$$

Step f5 next takes place. If the step of adjustment 5 continues at the end of step f5, a third acquisition of step 511 is carried out with a sphere value SPH2 of the adjusted set of parameters M2 which preferentially has a second positive variation compared to the starting sphere value SPH1, SPH1':

$$SPH2=(SPH1,SPH1')+k2 \text{ dioptre}$$

Step f5 next takes place. If the step of adjustment 5 continues at the end of step f5, a fourth acquisition of step 511 is carried out with a sphere value SPH2 of the adjusted set of parameters M2 which preferentially has a second negative variation compared to the starting sphere value SPH1, SPH1':

$$SPH2=(SPH1,SPH1')-k2 \text{ dioptre}$$

Step f5 next takes place. If the step of adjustment 5 is not terminated at the end of step f5, the step of adjustment 5 continues with the second sub-step 52.

During step 511, the values k1 and k2 of the first and second variations are preferentially selected from (0.50; 1.00; 1.50).

Each acquisition carried out during step 512 uses an adjusted set of parameters M2 for the optic, having:
a cylinder value CYL2 equal to the initial cylinder value CYL1, and
a cylinder axis value AX2 equal to the initial cylinder axis value AX1.

During the first acquisition of step 512, the sphere value SPH2 of the adjusted set of parameters M2 preferentially has a positive variation compared to the starting sphere value SPH1, SPH1':

$$SPH2=(SPH1,SPH1')+0.50 \text{ dioptre}$$

Step f5 described previously next takes place, which determines if the step of adjustment 5 continues or is terminated. If the step of adjustment 5 continues, a second acquisition of step 512 is made with a sphere value SPH2 of the adjusted set of parameters M2 which preferentially has a negative variation compared to the starting sphere value SPH1, SPH1':

$$SPH2=(SPH1,SPH1')-0.50 \text{ dioptre}$$

Step f5 next takes place. If the step of adjustment 5 is not terminated at the end of step f5, the step of adjustment 5 continues with the second sub-step 52.

The second sub-step 52 preferentially comprises a test T7 according to which the calculator answers the question: is the initial cylinder value CYL1, low, medium or high?

If the answer is "low", a step 520 is carried out according to which the initial cylinder value CYL1 and the initial cylinder axis value AX1 are compared with an expected total value ATA for these two values. A test T8 is next carried out according to which the calculator answers the question: "has the initial cylinder value CYL1 a power difference greater than or equal to x dioptre with its expected total value ATA, and/or has the initial cylinder axis value AX1 a difference greater than or equal to y° with its expected total value ATA?". Within the scope of the criterion applied during test T8, the value of x dioptre preferentially belongs to the interval [0.75 dioptre; 1.25 dioptre] and is more preferentially equal to 0.75 dioptre. The value of y° preferentially belongs to the interval [20°; 25°] and is more preferentially equal to 25°.

if the answer is no, the second sub-step 52 and the step of adjustment 5 are terminated. The method 100 continues with step 10 described previously, if the answer is yes, a step 521 is carried out according to which an acquisition is made of an adjusted visual acuity value AVA of the eye, using the expected total value ATA for the cylinder and the axis of the optic. Step f5 described previously is next carried out. In this particular case, if the step of adjustment 5 does not end in the course of step f5, the remainder "s5" of the step of adjustment 5 takes place but also corresponds to the end of the step of adjustment 5, then the intermediate assessment method 100 continues with step 10 described previously.

If the answer is "medium", a step 522 is carried out according to which at the most two acquisitions of an adjusted visual acuity value AVA of the eye are made, by varying the axis value of the optic compared to the initial cylinder axis value AX1. The second sub-step 52 is next terminated and the step of adjustment 5 continues with the third sub-step 53.

If the answer is "high", a test T9 is carried out according to which the calculator answers the question: is the starting sphere value SPH1, SPH1' strictly greater than the initial cylinder value CYL1?

if the answer is yes, a step 523 is carried out according to which at the most four acquisitions of an adjusted visual acuity value AVA of the eye are made, by varying the sphere value of the optic compared to the starting sphere value SPH1, SPH1'. The second sub-step 52 is next terminated and the step of adjustment 5 continues with the third sub-step 53.

if the answer is no, step 520 described previously is carried out, according to which the initial cylinder value CYL1 and the initial cylinder axis value AX1 are compared with the expected total value ATA for these two values. A test T8' is next carried out according to which the calculator answers the question: "has the initial cylinder value CYL1 a power difference greater than or equal to x' dioptre with its expected total value ATA, and/or has the initial cylinder axis value AX1 a difference greater than or equal to y'° with its expected total value ATA?". Within the scope of the criterion applied during test T8', the value of x' dioptre preferentially belongs to the interval [1 dioptre; 2 dioptres] and is more preferentially equal to 1.50 dioptre. The value of y'° preferentially belongs to the interval [20°; 25°] and is more preferably equal to 20°.

if the answer is no, the second sub-step 52 and the step of adjustment 5 are terminated. The method 100 continues with step 10 described previously.

if the answer is yes, step 521 described previously is carried out, according to which an acquisition is made of an adjusted visual acuity value AVA of the eye, using the expected total value ATA for the cylinder and the axis of the optic. Step f5 described previously is next carried out. In this particular case, if the step of adjustment 5 does not end in the course of step f5, the remainder "s5" of the step of adjustment 5 takes place and corresponds to the third sub-step 53.

The expected total value ATA for the cylinder and the axis is typically obtained by combining a first "corneal" component comprising a cylinder value (−CYLK) and a cylinder axis value AXK, the corneal component being obtained using a keratometer, with a second "internal" component having a cylinder value of −0.50 dioptre and a cylinder axis value of 90°. The expected total value ATA for the cylinder is thus equal to the combination of the corneal cylinder (−CYLK)AXK and the internal cylinder estimated at (−0.50 dioptre 90°).

Each acquisition carried out during step 522 uses an adjusted set of parameters M2 for the optic, having:
a sphere value SPH2 equal to the starting sphere value SPH1, SPH1', and
a cylinder value CYL2 equal to the initial cylinder value CYL1.

During the first acquisition of step 522, the cylinder axis value AX2 of the adjusted set of parameters M2 preferentially has a variation of +10° compared to the initial cylinder axis value AX1:

$$AX2=AX1+10°$$

Step f5 described previously next takes place, which determines if the step of adjustment 5 continues or is terminated. If the step of adjustment 5 continues, a second acquisition of step 522 is made with a cylinder axis value AX2 of the adjusted set of parameters M2 which preferentially has a variation of −10° compared to the initial cylinder axis value AX1:

$$AX2=AX1-10°$$

Step f5 next takes place. If the step of adjustment 5 is not terminated at the end of step f5, the step of adjustment 5 continues with the third sub-step 53.

Each acquisition carried out during step 523 uses an adjusted set of parameters M2 for the eye having:
a cylinder value CYL2 equal to the initial cylinder value CYL1, and
a cylinder axis value AX2 equal to the initial cylinder axis value AX1.

During the first acquisition of step 523, the sphere value SPH2 of the adjusted set of parameters M2 preferentially has a first positive variation compared to the starting sphere value SPH1, SPH1':

$$SPH2=(SPH1,SPH1')+k1 \text{ dioptre}$$

Step f5 described previously next takes place, which determines if the step of adjustment 5 continues or is terminated. If the step of adjustment 5 continues, a second acquisition of step 523 is carried out with a sphere value SPH2 of the adjusted set of parameters M2 which preferentially has a first negative variation compared to the starting sphere value SPH1, SPH1':

$$SPH2=(SPH1,SPH1')-k1 \text{ dioptre}$$

Step f5 next takes place. If the step of adjustment 5 continues at the end of step f5, a third acquisition of step 523 is made with a sphere value SPH2 of the adjusted set of parameters M2 which preferentially has a second positive variation compared to the starting sphere value SPH1, SPH1':

$$SPH2=(SPH1,SPH1')+k2 \text{ dioptre}$$

Step f5 next takes place. If the step of adjustment 5 continues at the end of step f5, a fourth acquisition of step 523 is made with a sphere value SPH2 of the adjusted set of parameters M2 which preferentially has a second negative variation compared to the starting sphere value SPH1, SPH1':

$$SPH2=(SPH1,SPH1')-k2 \text{ dioptre}$$

Step f5 next takes place. If the step of adjustment 5 is not terminated at the end of step f5, the step of adjustment 5 continues with the third sub-step 53. During step 523, the values k1 and k2 of the first and second variations are preferentially selected from (0.50; 1.00; 1.50).

If the second sub-step 52 is terminated with step 521, the third sub-step 53 comprises step 523 described previously, according to which at the most four acquisitions are made of an adjusted visual acuity value AVA of the eye, by varying the sphere value of the optic compared to the starting sphere value SPH1, SPH1'. The third sub-step 53 and the step of adjustment 5 are next terminated. The intermediate assessment method 100 continues with step 10 described previously.

If the second sub-step 52 is terminated with step 522, the third sub-step 53 firstly comprises step 520 described previously, according to which the initial cylinder value CYL1 and the initial cylinder axis value AX1 are compared with the expected total value ATA for these two values. A test T8" is next carried out, according to which the calculator answers the question: "has the initial cylinder value CYL1 a power difference greater than or equal to x" dioptre with its expected total value ATA, and/or has the initial cylinder axis value AX1 a difference greater than or equal to y"° with its expected total value ATA?". Within the scope of the criterion applied during test T8", the value of x" dioptre preferentially belongs to the interval [1 dioptre; 1.50 dioptre] and is more preferentially equal to 1.00 dioptre. The value of y"° preferentially belongs to the interval [15°; 20°] and is more preferentially equal to 15°.

If the answer is no, the third sub-step 53 and the step of adjustment 5 are terminated and the intermediate assessment method 100 continues with step 10 described previously.

If the answer is yes, step 521 described previously is carried out, according to which an acquisition is made of an adjusted visual acuity value AVA of the eye, using the expected total value ATA for the cylinder and the axis of the optic. Step f5 described previously is next carried out. In this particular case, if the step of adjustment 5 does not end in the course of step f5, the remainder "s5" of the step of adjustment 5 takes place but also corresponds to the end of the step of adjustment 5, then the intermediate assessment method 100 continues with step 10 described previously.

If the second step 52 is terminated with step 523, the third sub-step 53 firstly comprises step 520 described previously, according to which the initial cylinder value CYL1 and the initial cylinder axis value AX1 are compared with the expected total value ATA for these two values. Test T8' described previously is next carried out, according to which the calculator answers the question: has the initial cylinder value CYL1 a power difference greater than or equal to x' dioptre with its expected total value, and/or has the initial cylinder axis value AX1 a difference greater than or equal to y'° with its expected total value ATA?

If the answer is no, the third sub-step 53 and the step of adjustment 5 are terminated and the intermediate assessment method 100 continues with step 10 described previously.

If the answer is yes, step 521 described previously is carried out, according to which an acquisition is made of an adjusted visual acuity value AVA of the eye, using the expected total value ATA for the cylinder and the axis of the optic. Step f5 described previously is next carried out. In this particular case, if the step of adjustment 5 does not end in the course of step f5, the remainder "s5" of the step of adjustment 5 takes place but also corresponds to the end of the step of adjustment 5, then the intermediate assessment method 100 continues with step 10 described previously.

Within the scope of the present invention, it is preferentially considered that:

the initial cylinder value CYL1 is "low" if it is such that:

$$|CYL1|<1,00 \text{ dioptre}$$

the initial cylinder value CYL1 is "medium" if it is such that:

$$1.00 \text{ dioptre} \leq |CYL1| < 3.00 \text{ dioptres}$$

the initial cylinder value CYL1 is "high" if it is such that:

$$|CYL1| \geq 3.00 \text{ dioptres}$$

Within the scope of the present invention, when the starting sphere value SPH1, SPH1' is negative, it is preferentially considered that:

the starting sphere value SPH1, SPH1' is "low" if it is such that:

$$-0.25 \text{ dioptre} \leq SPH1, SPH1' \leq -2.50 \text{ dioptres}$$

the starting sphere value SPH1, SPH1' is "high" if it is such that:

$$SPH1, SPH1' < -2.50 \text{ dioptres}$$

Within the scope of the present invention, when the starting sphere value SPH1, SPH1' is positive, it is preferentially considered that:

the starting sphere value SPH1, SPH1' is "low" if it is such that:

$$0 \text{ dioptre} \leq SPH1, SPH1' \leq 2.50 \text{ dioptres},$$

the starting sphere value SPH1, SPH1' is "high" if it is such that:

$$SPH1, SPH1' > 2.50 \text{ dioptres}$$

Within the scope of the present invention and alternatively to the preceding paragraph, when the starting sphere value SPH1, SPH1' is positive, the starting sphere values SPH1, SPH1' defining the categories "low" and "high" are preferentially chosen as a function of the "low", "medium" or "high" categories of the initial cylinder value CYL1. Thus:

when the initial cylinder value CYL1 is "low", the starting sphere value SPH1, SPH1' is "low" if it is such that:

$$0 \text{ dioptre} \leq SPH1, SPH1 \leq +2.50 \text{ dioptres}$$

and the starting sphere value SPH1, SPH1' is "high" if it is such that:

$$SPH1, SPH1' > +2.50 \text{ dioptres}$$

when the initial cylinder value CYL1 is "medium", the starting sphere value SPH1, SPH1' is "low" if it is such that:

0 dioptre≤$SPH,SPH1$≤+3.00 dioptres and the starting sphere value SPH1, SPH1' is "high" if it is such that:

$SPH1,SPH1'$>+3.00 dioptres when the initial cylinder value CYL1 is "high", the starting sphere value SPH1, SPH1' is "low" if it is such that:

0 dioptre≤$SPH,SPH1$≤+2,00 dioptres, and the starting sphere value SPH1, SPH1' is "high" if it is such that:

$SPH1,SPH1'$>+2,00 dioptres

The intermediate assessment method 100 that has been described is advantageously followed by a full assessment method 200 which will now be described, in relation with FIGS. 1, 2c and 3. The full assessment method 200 is a subjective refraction measurement which typically comprises:
 a monocular test step 7 which is carried out firstly for one eye then for the other eye,
 a biocular test step 8 which is carried out for both eyes together, and
 a binocular test step 9 which is carried out for both eyes together.

The subjective measurement may be carried out in accordance with the prior art, which is for example described in the following works: "Borish's Clinical Refraction (2$^{nd}$ edition)" by William J. Benjamin (2006), and "Primary Care Optometry (5th edition)" by Theodore Grosvenor (2007).

FIG. 2c shows that when step f5 ends the step of adjustment 5 and the intermediate assessment method 100, it is advantageously followed by the full assessment method 200. More specifically, it is advantageously followed by the monocular step of test 7 (representation in dotted lines in FIG. 3).

Figure 3:
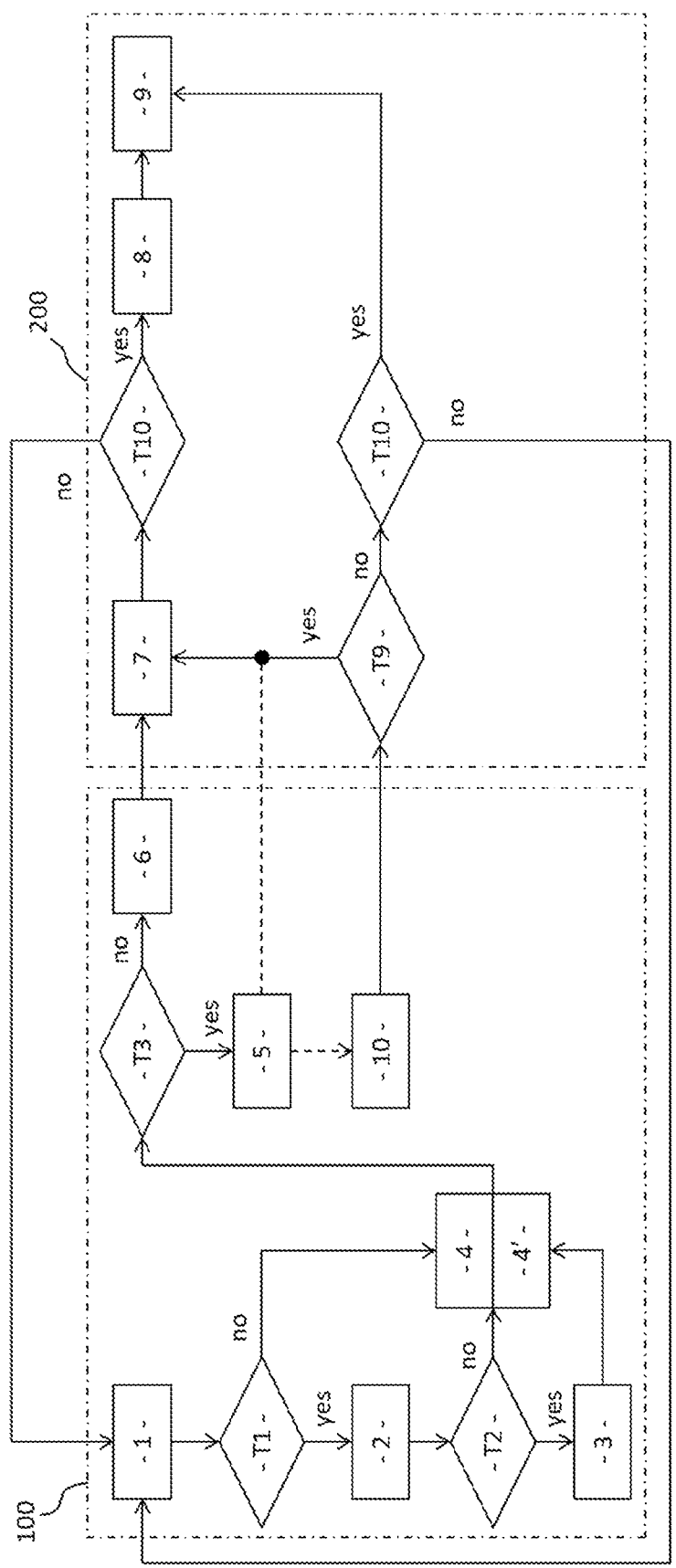
FIG. 3 shows a schematic representation of a method comprising the intermediate assessment of FIG. 1a followed by a full assessment.

FIG. 3 shows that when the answer to the question of test T3, "is the modified visual acuity value AVM, AVM' of the eye strictly less than the reference visual acuity value AVR of the eye?", is "no", test T3 is advantageously followed by the accommodation step of verification 6 then by the monocular step of test 7.

FIG. 3 shows that step 10, according to which an acquisition is made of a visual acuity value of the eye by arranging in front of the eye an optic which is a pinhole disk, is advantageously followed by a step of test T9, according to which the calculator answers the question: is the visual acuity better or identical with the pinhole disk?
 If the answer is yes, the monocular step of test 7 is carried out.
 If the answer is no, test T10 described previously is carried out, according to which the calculator answers the question: "has the intermediate assessment method 100 been performed for both eyes?". If the answer is "no", the calculator loops back to step 1 of the intermediate assessment method 100, for the second eye. If the answer is "yes", the test T10 is followed by the binocular step of test 9.

The monocular test step 7 is followed by a step of test T10, according to which the calculator answers the question: "has the intermediate assessment method 100 been performed for both eyes?". If the answer is "no", the calculator loops back to step 1 of the intermediate assessment method 100, for the second eye. If the answer is "yes", the test T10 is followed by the biocular step of test 8, then by the binocular step of test 9.

The invention claimed is:

1. Method for intermediate assessment of an eye of a user comprising:
 a step of attributing to the eye of the user a reference visual acuity value AVR, as a function of the age of the user and an initial set of parameters M1 of the eye comprising an initial sphere value SPH1, an initial cylinder value CYL1 and an initial cylinder axis value AX1, and by means of a matrix having a plurality of L lines and a plurality of C columns and thus comprising L×C components, each line corresponding to a set of parameters category, each column corresponding to an age category and each component being associated with a reference visual acuity value AVR;
 when the sphere value SPH1 of the initial set M1 is such that:

5.00 dioptres≤$SPH1$≤3.00 dioptres, a step of acquisition of a raw visual acuity value AVB of the eye;
 when the raw visual acuity value AVB has been measured previously and when it is greater than a reference raw visual acuity value AVBR, a step of weighting the initial set of parameters M1 to obtain a weighted set of parameters M1' having the initial cylinder value CYL1, the initial cylinder axis value AX1 and a weighted sphere value SPH1' such that:

$SPH1+0.25≤SPH1'≤SPH1+0.75$ dioptre;

a step of acquisition of a modified visual acuity value AVM, AVM' of the eye, by arranging in front of the eye an optic having the initial set of parameters M1 or, if the step of obtaining a weighted set of parameters M1' has been performed, then arranging in front of the eye an optic having the weighted set of parameters M1';
 when the modified visual acuity value AVM, is strictly less than the reference visual acuity value AVR, a step of adjustment comprising at least one acquisition of an adjusted visual acuity value AVA of the eye, by arranging in front of the eye an optic having an adjusted set of parameters M2.

2. The method according to claim 1, wherein after each acquisition of an adjusted visual acuity value AVA of the eye, when the adjusted visual acuity value AVA measured for the eye is greater than or equal to the reference visual acuity value AVR, the step of adjustment ends.

3. The method according to claim 1, wherein when, with an optic having a set of parameters of which the sphere value has a positive variation compared to the preceding tested sphere value, or of which the axis value has a variation compared to the preceding tested axis value, or of which the cylinder and axis values correspond respectively to an expected total value ATA, the adjusted visual acuity value AVA acquired for the eye is greater than or equal to the reference visual acuity value AVR, then the method comprises a step according to which an acquisition is made of a visual acuity value of the eye by increasing by +0.75 dioptre the sphere value of the optic.

4. The method according to claim 1, wherein the step of adjustment comprises a first sub-step in which a low or medium cylinder category and a high cylinder category, a low sphere category and a high sphere category are distinguished, and according to which:

when the cylinder is high, at the most four acquisitions are made of an adjusted visual acuity value AVA of the eye by varying the cylinder axis value of the optic;

when the cylinder is low or medium and if the sphere is high, at the most four acquisitions are made of an adjusted visual acuity value AVA of the eye by varying the sphere value of the optic;

when the cylinder is low or medium and if the sphere is low, at the most two acquisitions are made of an adjusted visual acuity value AVA of the eye by varying the sphere value of the optic.

5. The method according to claim 4, wherein the step of adjustment comprises a second sub-step such that:

when the cylinder is low, a comparison is made of the cylinder and the axis with an expected total value ATA respectively for the cylinder and the axis;

when the cylinder has a power difference greater than or equal to 0.75 dioptre with its expected total value ATA and/or when the axis has a difference greater than or equal to 25° with its expected total value ATA, then an acquisition is made of an adjusted visual acuity value AVA of the eye using the expected total value ATA for the cylinder and the axis of the optic;

when the cylinder is medium, at the most two acquisitions are made of an adjusted visual acuity value AVA of the eye by varying the axis value of the optic;

when the cylinder is high and when the sphere value SPH1 or weighted sphere value SPH1' is strictly greater than the cylinder value CYL1, at the most four acquisitions are made of an adjusted visual acuity value AVA of the eye by varying the sphere value of the optic;

when the cylinder is high and when the sphere value SPH1 or weighted sphere value SPH1' is less than or equal to the cylinder value CYL1, a comparison is made of the cylinder and the axis with the expected total value ATA for the cylinder and the axis; when the cylinder has a power difference greater than or equal to 1.50 dioptres with its expected value ATA and/or when the axis has a difference greater than or equal to 20° with its expected total value ATA, then an acquisition is made of an adjusted visual acuity value AVA of the eye using the expected total value ATA for the cylinder and the axis of the optic.

6. The method according to claim 5, wherein when the cylinder is low, the step of adjustment is terminated at the end of the first and second sub-steps, if not the step of adjustment comprises a third sub-step such that:

when the cylinder is medium, a comparison is made of the cylinder and the axis with their expected total value ATA; when the cylinder has a power difference greater than or equal to 1.00 dioptre with its expected total value ATA and/or when the axis has a difference greater than or equal to 15° with its expected total value ATA, then an acquisition is made of an adjusted visual acuity value AVA of the eye using the expected total value ATA for the cylinder and the axis of the optic;

when the cylinder is high and when the sphere value SPH1 or weighted sphere value SPH1' is strictly greater than the cylinder value CYL1, a comparison is made of the cylinder and the axis with their expected total value ATA; when the cylinder has a power difference greater than or equal to 1.50 dioptres with its expected total value ATA and/or if when the axis has a difference greater than or equal to 20° with its expected total value ATA, then an acquisition is made of an adjusted visual acuity value AVA of the eye using the expected total value ATA for the cylinder and the axis of the optic;

when the cylinder is high and when the sphere value SPH1 or weighted sphere value SPH1' is less than or equal to the cylinder value CYL1, at the most four acquisitions are made of an adjusted visual acuity value AVA of the eye by varying the sphere value of the optic.

7. A non-transitory computer readable medium comprising software instructions which, when the software instructions are executed by a computer, implement the method according to claim 1.

8. Device for intermediate assessment of an eye comprising:

a memory for storing a matrix having a plurality of L lines and a plurality of C columns and thus comprising L×C components, each line corresponding to a set of parameters category, each column corresponding to an age category and each component being associated with a reference visual acuity value AVR, a memory for storing a set of parameters comprising a sphere value, a cylinder value and a cylinder axis value, a plurality of optics, a means for arranging an optic of the plurality of optics in front of the eye, a display means, a means for acquiring visual acuity values of the eye, a memory for storing an acquired visual acuity value, a calculator comprising means for carrying out the steps of the method for intermediate assessment of an eye according to claim 1.

* * * * *